US012594272B2

(12) United States Patent
Turnbull

(10) Patent No.: US 12,594,272 B2
(45) Date of Patent: Apr. 7, 2026

(54) 2-BROMO-LYSERGIC ACID DIETHYLAMIDE FOR SUBSTANCE ABUSE

(71) Applicant: CERUVIA LIFESCIENCES LLC, Greewich, CT (US)

(72) Inventor: Carey Turnbull, Greenwich, CT (US)

(73) Assignee: Ceruvia Lifesciences LLC, Greenwich, CT (US)

( * ) Notice: Subject to any disclaimer, the term of this patent is extended or adjusted under 35 U.S.C. 154(b) by 660 days.

(21) Appl. No.: 17/913,471

(22) PCT Filed: Mar. 25, 2021

(86) PCT No.: PCT/US2021/024229
§ 371 (c)(1),
(2) Date: Sep. 22, 2022

(87) PCT Pub. No.: WO2021/195427
PCT Pub. Date: Sep. 30, 2021

(65) Prior Publication Data
US 2023/0133108 A1     May 4, 2023

Related U.S. Application Data

(60) Provisional application No. 62/994,590, filed on Mar. 25, 2020.

(51) Int. Cl.
A61K 31/48       (2006.01)
A61P 25/32       (2006.01)

(52) U.S. Cl.
CPC .............. A61K 31/48 (2013.01); A61P 25/32 (2018.01)

(58) Field of Classification Search
CPC ................................ A61K 31/48; A61P 25/32
See application file for complete search history.

(56) References Cited

U.S. PATENT DOCUMENTS

| | | |
|---|---|---|
| 2013/0252996 A1 | 9/2013 | Halpern et al. |
| 2018/0021334 A1 | 1/2018 | Marchant et al. |
| 2018/0185375 A1 | 7/2018 | Detke et al. |
| 2020/0030309 A1 | 1/2020 | Olson |

OTHER PUBLICATIONS

Bogenschutz et al., Current Topics in Behavioral Neurosciences vol. 36 (2018): Chapter: Therapeutic Applications of Classic Hallucinogens, pp. 361-391. (Year: 2018).*
Karst et al., Cephalagia, vol. 30 (9), pp. 1140-1144. (Year: 2010).*
Spirtes et al., A Central Nervous System Effect of a Non-Hallucinatory Lysergic Acid Derivative, Experientia 1958, vol. XIV, p. 428. (Year: 1958).*

* cited by examiner

*Primary Examiner* — Amy L Clark
*Assistant Examiner* — Janet L Coppins
(74) *Attorney, Agent, or Firm* — Kohn & Associates PLLC; Kenneth I. Kohn; Laura S. Dellal

(57)         ABSTRACT

A method of treating substance abuses in an individual, by administering 2-bromo-lysergic acid diethylamide (BOL-148) to an individual and reducing use of the substance.

6 Claims, No Drawings

2-BROMO-LYSERGIC ACID DIETHYLAMIDE FOR SUBSTANCE ABUSE

BACKGROUND OF THE INVENTION

1. Technical Field

The present invention relates to compositions and methods for treating substance abuses, and especially alcohol use disorder (AUD). More specifically, the present invention relates to methods of using 2-bromo-lysergic acid diethylamide (BOL-148) in treating substance abuses.

2. Background Art

Alcohol use disorder (AUD) is a disease that is generally characterized by compulsive alcohol use, loss of control over alcohol intake, and a negative emotional state when not using. This disease affects about 15 million people in the United States, including adolescents and adults, as well as their families.

Several types of treatment are available for AUD. Behavioral treatments such as counseling can help change an individual's drinking behavior, such as providing coping mechanisms and suggesting the individual avoid triggers that cause drinking. There are also many support groups such as Alcoholics Anonymous that provide peer support to help individuals to stop drinking. Medications can also be prescribed to help stop or reduce drinking.

Naltrexone is drug that acts as a competitive antagonist at the μ-opioid receptor that is prescribed to manage alcohol or opioid dependence. Naltrexone can decrease the amount and frequency of drinking; however, it seems to only have a modest effect on AUD. In treating AUD, it is taken orally about an hour before drinking to avoid side effects. Naltrexone blocks the positive-reinforcement effects of alcohol. It can decrease cravings for opioids as well after a few weeks and can decrease risk of overdose. For this indication, naltrexone is injected once a month. There are several side effects, including diarrhea, abdominal cramping, liver damage, trouble sleeping, anxiety, nausea, and headaches.

Acamprosate stabilizes chemical signaling in the brain that would otherwise be disrupted by alcohol withdrawal. It has not been found to be effective alone and requires psychosocial support. Side effects include allergic reactions, abnormal heart rhythms, low or high blood pressure, diarrhea, headaches, insomnia, and impotence. Major side effects can include suicidal behavior, major depressive disorder, and kidney failure.

Disulfiram produces an acute sensitivity to ethanol by inhibiting the enzyme acetaldehyde dehydrogenase. This effectively produces a hangover effect immediately after drinking. Side effects include flushing, throbbing in the head and neck, headaches, respiratory difficulty, nausea, vomiting, sweating, thirst, chest pain, palpitations, dyspnea, hyperventilation, fast heart rate, low blood pressure, fainting, uneasiness, weakness, vertigo, blurred vision, and confusion. Severe side effects include respiratory depression, cardiovascular collapse, abnormal heart rhythms, heart attack, acute congestive heart failure, unconsciousness, convulsions, and death.

Other drugs that are used for other indications can also be helpful in treating AUD, including varenicline (anti-smoking), gabapentin (pain and epilepsy), topiramate (anti-epileptic).

Hallucinogenic drugs have also been investigated in treating AUD or other addictions. Bogenschutz, et al. (Journal of Psychopharmacology 2015, Vol. 29(3) 289-299) examined in a pilot study ten volunteers with DSM-IV alcohol dependence who received orally administered psilocybin in one or two supervised sessions in addition to Motivational Enhancement Therapy and therapy sessions devoted to preparation for and debriefing from the psilocybin sessions. Participants' responses to psilocybin were qualitatively similar to those described in other populations. Abstinence did not increase significantly in the first 4 weeks of treatment (when participants had not yet received psilocybin) but increased significantly following psilocybin administration (p<0.05). Gains were largely maintained at follow-up to 36 weeks.

Dipropyltryptamine (DPT) has also been investigated in the treatment of alcoholism. In a single-group pilot study involving 51 participants, Grof et al. (1973) reported highly significant improvement in clinical outcomes including abstinence among the 47 participants (92%) who received between 1 and 6 DPT (mean 1.9) sessions and completed follow-up at 6 months. However, a subsequent trial comparing DPT treatment with conventional treatment found no significant differences between DPT-treated participants and the other groups in clinical outcomes assessed at 6 month follow-up, and conventional treatment group members assessed at 12 months reported better drinking outcomes and social functioning than the other two groups. Therefore, it is not clear that all hallucinogens can treat alcohol abuse.

Alper, et al. (Frontiers in Pharmacology, 31 Aug. 2018) showed that mice treated with 25 μg/kg LSD had reduced ethanol consumption (group mean reduction of 17.9%) relative to controls. This effect was shown for 46 days of observation. However, LSD is a schedule I drug that is not approved for any medical use, making it impossible to prescribe to those who need treatment of AUD. Moreover, LSD induces powerful temporary consciousness-altering ('psychedelic') effects that render its delivery to human patients logistically challenging. The mechanism of action underlying this LSD-induced reduction in alcohol preference remains unclear. Existing (approved) treatments for AUD described above are not psychedelic, and their mechanisms of action are each distinct from effects known to be produced by psychedelic compounds.

LSD has known effects at several types of receptors, such as dopamine receptors, adrenergic receptors, and serotonin receptors (5HT) 1A, 2A, 5C, and 6. LSD is a potent agonist of 5HT1A receptors (Aghajanian G K. (1995): Electrophysiology of serotonin receptor subtypes and signal transduction mechanisms. In Bloom F E, Kupfer D J (eds), *Psychopharmacology: The Fourth Generation of Progress*. New York, Raven Press, pp 451-460), a partial agonist of 5HT2A receptors (i.e., not as strong of an agonist, Marek, et al., J Pharmacol Exp Ther. 1996 September; 278(3):1373-82), and a partial agonist of dopamine receptors (Giacomelli, et al. Life Sci. 1998; 63(3):215-22). 5HT2A receptors are involved in hallucinogenic effects. Pierce, et al. state that "data from radioligand binding, cellular, smooth muscle, and behavioral studies . . . suggest that d-LSD is a potent 5-HT2 antagonist." (Neuropsychopharmacology. October-December 1990; 3(5-6):503-8.) The belief that LSD was an antagonist likely was because it is actually a partial agonist at certain receptors versus an agonist. This shows that there was much unknown about LSD in early studies, and that statements and experiments done in the past are not necessarily predictive of knowledge at the current time.

2-Bromo-LSD (also called BOL-148) is a derivative of LSD that is inactive as a psychedelic (and not scheduled) but also has an effect on 5-HT receptors as a neutral antagonist (i.e., it occupies a receptor binding site but does not induce constitutive receptor activity). BOL-148 having halogenation at the 2-position of LSD provides 5HT2A antagonist activity (Sagar et al. A Brief Review of Chemistry and Pharmacology of Lysergic Acid Diethylamide. Research J. Pharm. and Tech 2017; 10(12): 4415-4422). Jadhav, et al. (*A Brief Review of Chemistry and Pharmacology of Lysergic Acid Diethylamide. Research J. Pharm. and Tech* 2017; 10(12): 4415-4422.) state that "Pre-treatment with BOL-148, a non-hallucinogenic congener of LSD with serotonin antagonist properties like LSD, will not block the effects of LSD" with regards to experiments in rats. This statement should be interpreted that LSD has a higher affinity for 5-HT2A receptors than BOL-148 and can displace BOL from occupied receptors in rats, as Jadhav, et al. clearly state that LSD itself is a 5-HT2A agonist. Nichols, et al. states regarding humans that "Although virtually no work has been done with BOL-148 since the early 1970s, it was demonstrated early on that it could block the effects of LSD in humans" (WIREs Membr Transp Signal 2012, 1:559-579).

U.S. Pat. No. 8,883,808 to Bonavanture, et al. discloses administering effective amounts of an SRI and a 5-HT7 receptor antagonist to a subject to treat serotonin-mediated diseases and conditions (or their associated symptoms) that are mediated through increasing the release of serotonin, inhibiting its reuptake, or both, or by increasing activity of serotonergic neurons, such as those associated with aberrant 5-HT7 receptor levels or serotonin reuptake activity or function. The 5-HT7 antagonist can be 2-Br LSD (BOL-148). One such disease can be alcohol abuse. There is no disclosure of using the 5-HT7 receptor antagonist without being in combination with an SRI. There is much support for the involvement of 5-HT2A and downstream neuroplasticity-related events that it can trigger underlying anti-addictive effects of other 2A agonists (e.g., psilocybin), that the effects of any one of these compounds are unlikely to be due to actions at 5HT7 alone.

Assays can be performed to find agents that bind or inhibit binding to serotonin receptors. For example, U.S. Pat. No. 6,844,190 to Sibley, et al. discloses isolating mammalian serotonin receptor protein St-B17 and using it in an assay for screening drug candidates. Br-LSD (BOL-148) was tested in displacing LSD.

There have been no studies previously performed investigating treating AUD with BOL-148 or providing dosing in humans. While many treatments are available for AUD, there remains a need for a treatment with fewer side effects as well as for a medication that is readily available.

SUMMARY OF THE INVENTION

The present invention provides for a method of treating substance abuses in an individual, by administering 2-bromo-lysergic acid diethylamide (BOL-148) to an individual and reducing use of the substance.

DETAILED DESCRIPTION OF THE INVENTION

The present invention generally provides for a method of treating substance abuses in an individual, by administering 2-bromo-lysergic acid diethylamide (BOL-148) to an individual and reducing use of the substance. BOL-148 can work in reducing substance use in a similar manner to LSD by its effects at the 5HT2A receptor, further described below.

Reducing use of the substance can include reducing frequency of use, reducing an amount of substance used, and/or stopping use of the substance.

The substance abuse can be, but is not limited to alcohol, cocaine, nicotine, opiates, or any other substance that can be abused. In other words, an individual can be treated for using substances such as cocaine, nicotine, opiates, alcohol, morphine, methamphetamine, or other substances. Behavioral disorders can also be treated in the present invention.

Doses of BOL-148 used in an initial rodent study are 0.03 mg/kg and 3.0 mg/kg, which is equivalent to 0.75 µg (7.5 mg×10$^{-4}$ mg) and 75 µg (0.075 mg) for an average mouse weighing 25 g (0.025 kg). For an average human weighing 70 kg, equivalent doses are 2.1 mg and 210 mg, respectively. Therefore, a dose of 2.1 to 210 mg can be used in humans. The lower dose of BOL-148 used in this trial is equivalent (0.03 mg/kg) on a per-weight basis to a dose shown to be effective at reducing cluster headaches when delivered daily to human participants in an open-label compassionate use trial (Karst et al., Cephalalgia. 2010 September; 30(9):1140-4).

Administration can be hourly, daily, weekly, or longer periods of time.

The compound of the present invention is administered and dosed in accordance with good medical practice, considering the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants, and vehicles. The compounds can be administered orally, subcutaneously, or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants, and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

EXAMPLE 1

Materials and Methods

Animals

All experiments will be conducted in adult male C57BL/6J mice (10-18 weeks old; Jackson Laboratory, United States). Mice will be given unlimited access to standard mouse chow and water throughout the entire study.

Ethanol Drinking Behavior

The effect of BOL-148 on ethanol consumption will be assessed using a two-bottle choice drinking paradigm. Mice will be housed singly and habituated to reverse light-dark cycle for at least a week. The mice will be then exposed to ethanol to develop preference with two bottles containing water and 20% ethanol offered for 24 hours in the beginning of the dark phase for five days a week (Monday through Friday) for 4 weeks. The mice will be then divided into three groups of equal ethanol intake based on the amount of ethanol consumed on the day before administration of either saline or BOL-148 (0.3 mg/kg, or 3.0 mg/kg IP; approximately 9 µg and 90 µg for an average 30 g mouse) once before the onset of the dark cycle. BOL-148 will be supplied by the NIDA Drug Supply Program, Bethesda, MD, United States. Water bottles will be replaced with bottles containing water and ethanol after 10 minutes of treatment. Amounts of ethanol and water consumption will be measured every 24 hours. The positions of water and ethanol bottles will be alternated every day to avoid place preference. Two bottles containing water and 20% ethanol will be placed in a cage without a mouse to control for spillage and evaporation.

Locomotor Activity

Ambulatory activity will be measured as ambulatory counts (interruption of the total number of beams, on both the x and y-axis) with an infrared beam-based activity sensor (ATM3; Columbus Instrument, Columbus, OH, United States) over a 24-hour period beginning at the dark cycle at 1 and 8 days after the administration of 3.0 mg/kg BOL-148 or saline to ethanol-naïve mice.

Statistical Analysis

Data will be analyzed using SPSS version 25 for Windows (IBM Corp., Armonk, N.Y., USA; released 2017), using repeated measures ANOVA (MIXED command), including treatment group, time (Day 1-42), and the interaction between time and treatment group as independent variables. Data will be analyzed separately for each of 3 dependent variables: ethanol consumption, ethanol preference (ethanol consumption/total fluid consumption), and total fluid consumption. Alpha level will be set at 0.05 for all comparisons.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method for treating substance abuse in an individual, in need thereof comprising administering 3.0 mg/kg of 2-bromo-lysergic acid diethylamide (BOL-148) to the individual and reducing the individual's use of the substance, wherein the substance is alcohol.

2. The method of claim 1, wherein reducing the individual's use of the substance comprises reducing the frequency of use, reducing the amount of substance used, stopping the use of the substance, or a combination thereof.

3. The method of claim 2, wherein reducing the individual's use of the substance comprises reducing the frequency of use.

4. The method of claim 2, wherein reducing the individual's use of the substance comprises reducing the amount of substance used.

5. The method of claim 2, wherein reducing the individual's use of the substance comprises stopping the use of the substance.

6. The method of claim 1, wherein BOL-148 is administered by injection to the individual at a time period selected from the group consisting of hourly, daily, and weekly.

\* \* \* \* \*